United States Patent
Spears et al.

(12)

(10) Patent No.: US 11,684,641 B2
(45) Date of Patent: Jun. 27, 2023

(54) COMPOSITIONS AND METHODS FOR DIGESTIVE HEALTH IN AN ANIMAL

(71) Applicant: Société des Produits Nestlé S.A., Vevey (CH)

(72) Inventors: Julie Kristine Spears, St. Louis, MO (US); Alison Beloshapka, St. Louis, MO (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 187 days.

(21) Appl. No.: 17/313,454

(22) Filed: May 6, 2021

(65) Prior Publication Data

US 2021/0369796 A1 Dec. 2, 2021

Related U.S. Application Data

(60) Provisional application No. 63/034,030, filed on Jun. 3, 2020, provisional application No. 63/032,033, filed on May 29, 2020.

(51) Int. Cl.

| | |
|---|---|
| *A61K 35/744* | (2015.01) |
| *A23K 50/40* | (2016.01) |
| *A23K 10/18* | (2016.01) |
| *A23K 10/30* | (2016.01) |
| *A61P 1/14* | (2006.01) |
| *A61K 9/00* | (2006.01) |
| *A61K 31/355* | (2006.01) |
| *A61K 31/375* | (2006.01) |
| *A61K 33/04* | (2006.01) |
| *A61K 33/18* | (2006.01) |
| *A61K 33/26* | (2006.01) |
| *A61K 33/30* | (2006.01) |
| *A61K 33/32* | (2006.01) |
| *A61K 33/34* | (2006.01) |
| *A61K 36/064* | (2006.01) |
| *A61K 36/68* | (2006.01) |

(52) U.S. Cl.
CPC .......... *A61K 35/744* (2013.01); *A23K 10/18* (2016.05); *A23K 10/30* (2016.05); *A23K 50/40* (2016.05); *A61K 9/0056* (2013.01); *A61K 31/355* (2013.01); *A61K 31/375* (2013.01); *A61K 33/04* (2013.01); *A61K 33/18* (2013.01); *A61K 33/26* (2013.01); *A61K 33/30* (2013.01); *A61K 33/32* (2013.01); *A61K 33/34* (2013.01); *A61K 36/064* (2013.01); *A61K 36/68* (2013.01); *A61P 1/14* (2018.01)

(58) Field of Classification Search
CPC ...................................................... A61K 35/744
See application file for complete search history.

(56) References Cited

U.S. PATENT DOCUMENTS

| | | |
|---|---|---|
| 6,303,355 B1 | 10/2001 | Opara |
| 6,887,493 B2 | 5/2005 | Shefer et al. |
| 6,969,530 B1 | 11/2005 | Curtis et al. |
| 6,974,592 B2 | 12/2005 | Yan |
| 2005/0153018 A1 | 7/2005 | Ubbink et al. |
| 2005/0266069 A1 | 12/2005 | Simmons et al. |
| 2007/0298013 A1 | 12/2007 | Altman |
| 2010/0266549 A1 | 10/2010 | Zink et al. |
| 2020/0085887 A1 | 3/2020 | Czarnecki-Maulden et al. |

FOREIGN PATENT DOCUMENTS

| | | | | |
|---|---|---|---|---|
| WO | WO-2007039313 A2 * | 4/2007 | ............ | A23K 10/18 |

OTHER PUBLICATIONS

English machine translation of Murakami, JP 2004-215561 A, 2004.*

Pace et al., "Modulations in the Offspring Gut Microbiome are Refractory to Postnatal Synbiotic Supplementation among Juvenile Primates", BMC Microbiology, vol. 18, Issue No. 1, Dec. 1, 2018, pp. 1-13, XP055819691.

Landes et al., "Fecal Sand Clearance Is Enhanced with a Product Combining Probiotics, Prebiotics, and Psyllium in Clinically Normal Horses", Journal of Equine Veterinary Science, vol. 28, Issue No. 2, Feb. 13, 2008, pp. 79-84, XP022506490.

Haghshenas et al., "Effect of Addition of Inulin and Fenugreek on the Survival of Microencapsulated Enterococcus Durans 39C in Alginate-Psyllium Polymeric Blends in Simulated Digestive System and Yogurt", Asian Journal of Pharmaceutical Sciences, vol. 10, Issue No. 4, Jul. 1, 2015, pp. 350-361, XP055453596.

International Search Report and Written Opinion to PCT/IB21/053870 dated Jul. 15, 2021.

* cited by examiner

*Primary Examiner* — Rosanne Kosson

(57) ABSTRACT

A method of improving microbiome within an animal can comprise administering to the animal a composition comprising a probiotic and *psyllium*, wherein the probiotic comprises at least one of any suitable strain or subspecies of *Enterococcus*. Compositions containing a probiotic and *psyllium* are also provided herein.

19 Claims, No Drawings

COMPOSITIONS AND METHODS FOR DIGESTIVE HEALTH IN AN ANIMAL

CROSS REFERENCE TO RELATED APPLICATION

This application claims the benefit of and priority to U.S. Provisional Application Ser. No. 63/034,030 filed Jun. 3, 2020 and U.S. Provisional Application Ser. No. 63/032,033 filed May 29, 2020, the disclosures of which are incorporated in their entireties herein by this reference.

BACKGROUND

The intestinal tract plays a critical role in animal health and wellness. To help fulfill this role, the intestinal tract contains various microorganisms that comprise a healthy gastrointestinal microflora under normal conditions. The microflora confers many benefits to the animal, e.g., the production of fatty acids that fuel the cells that line the gastrointestinal lumen, the synthesis of vitamins, and the synthesis of enzymes that aid in the breakdown and digestion of food. In addition, the microflora aids the immune system in host protection from disease. For example, microflora are known to inhibit the attachment to and colonization of potential pathogens within the gastrointestinal tract and to stimulate the production of cytokines and immunoglobulins.

Unfortunately, disruption of the normal balance of microflora can result in opportunistic infection of the gastrointestinal tract and can facilitate additional complications such as diarrhea and dehydration. The normal microflora balance can be disrupted through a variety of means, e.g., stress, advanced age, travel, consumption of contaminated food or water, antibiotic therapy, and the like. One method for preventing or treating such undesirable disruption involves prophylactically administering probiotics to an animal to prevent the disruption or to therapeutically administering probiotics to an animal to restore the normal microflora balance and facilitate recovery from the resulting undesirable complications caused by the disruption.

Probiotics and their benefits for animal health are well known to skilled artisans. Probiotics are live microorganisms that have a beneficial effect in the prevention and treatment of specific medical conditions when ingested. Probiotics are believed to exert biological effects through a phenomenon known as colonization resistance. Probiotics facilitate a process whereby the indigenous anaerobic flora limits the concentration of potentially harmful (mostly aerobic) bacteria in the digestive tract. Other modes of action, such as supplying enzymes or influencing enzyme activity in the gastrointestinal tract, may also account for some of the other functions that have been attributed to probiotics. Probiotics are known to enhance intestinal function, stimulate the immune system, reduce inflammation, and diminish the population of harmful microorganisms in the gastrointestinal tract.

While probiotics are generally useful for promoting the health of an animal, they are often difficult to store, handle, and administer to the animal. Probiotics may be unstable under normal environmental conditions and require special handling, e.g., refrigeration, freeze drying, or other means to prolong probiotic life. Similarly, probiotics are often unpalatable to the animal consuming them. Often, the palatability must be disguised or enhanced using other compounds or compositions. Further, it may be beneficial to supplement the immune system, particularly in the gastrointestinal tract, using ingredients in combination with the probiotics to obtain maximum benefit from probiotic administration. Additionally, achieving therapeutic amounts can be challenging. There is, therefore, a need for new compositions containing probiotics that can overcome these challenges.

SUMMARY

The present disclosure relates generally to pet food compositions; methods of improving microbiome in an animal; and methods for improving or treating gastrointestinal issues in animals. Additional embodiments include treating or preventing diarrhea, increasing or improving fecal quality, and increasing or improving digestive health.

In one embodiment, a pet food composition can comprise a probiotic comprising at least one of any suitable strain or subspecies of *Enterococcus*, and *psyllium* in an amount from about 20 weight % to about 80 weight %.

In another embodiment, a method of improving microbiome within an animal can comprise administering to the animal a composition comprising a probiotic and *psyllium*, wherein the probiotic comprises at least one of any suitable strain or subspecies of *Enterococcus*.

Other embodiments include treating or preventing diarrhea, increasing or improving fecal quality, and increasing or improving digestive health by administering the compositions described herein.

Additional features and advantages are described herein and will be apparent from the following Detailed Description.

DETAILED DESCRIPTION

Definitions

As used in this disclosure and the appended claims, the singular forms "a," "an" and "the" include plural referents unless the context clearly dictates otherwise. Thus, for example, reference to "a composition" or "the composition" includes two or more compositions. The term "and/or" used in the context of "X and/or Y" should be interpreted as "X," or "Y," or "X and Y." Where used herein, the terms "example" and "such as," particularly when followed by a listing of terms, are merely exemplary and illustrative, and are not exclusive or comprehensive.

The term "animal" means any animal that can benefit from the present compositions, including human, avian, bovine, canine, equine, feline, hircine, lupine, murine, ovine, or porcine animals. In one aspect, the animal can be a mammal. In another aspect, the animal can be a companion animal.

The term "companion animal" means domesticated animals such as cats, dogs, rabbits, guinea pigs, ferrets, hamsters, mice, gerbils, horses, cows, goats, sheep, donkeys, pigs, and the like. In one aspect, the companion animal can be a canine. In another aspect, the companion animal can be a feline.

As used herein, "about" is understood to refer to numbers in a range of numerals, for example the range of −10% to +10% of the referenced number, within −5% to +5% of the referenced number, or in one aspect, within −1% to +1% of the referenced number, and in a specific aspect, within −0.1% to +0.1% of the referenced number. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the total weight of the food composition unless expressed otherwise. When reference is made to the pH, values correspond to pH measured at 25° C. with standard equipment. An "amount" can be the total amount of the referenced component per serving of the composition or per distinct unit of the composition and/or can be the weight percentage of the referenced component by dry weight. Moreover, an "amount" includes zero; for example, the recitation of an amount of a compound does not necessarily mean that the compound is present, unless followed by a range that excludes zero.

The terms "pet food," "pet food product" and "pet food composition" mean a product or composition that is intended for ingestion by a canine or feline that provides at least one nutrient to the animal. Further in this regard, these terms mean that the product or composition is in a form ready for consumption and is not merely an intermediate from which a consumable product or composition is made, although other food compositions can be added in some embodiments, such as a dietary supplement. The term "pet food" means any food composition intended to be consumed by a canine or feline.

The term "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In one embodiment, the present probiotic and *psyllium* can be present in an effective amount for improving microbiome, improving or treating gastrointestinal issues, treating or preventing diarrhea, increasing or improving fecal quality, and/or increasing or improving digestive health.

The dosages expressed herein are in milligrams per kilogram of body weight per day (mg/kg/day) unless expressed otherwise.

The term "long-term administration" means periods of repeated administration or consumption in excess of one month. Periods of longer than two, three, or four months can be used for certain embodiments. Also, more extended periods can be used that include longer than 5, 6, 7, 8, 9, or 10 months. Periods in excess of 11 months or 1 year can also be used. Longer term use extending over 1, 2, 3, or more years are included in the invention. For certain aging canines, the canine will continue consuming on a regular basis for the remainder of its life. This can also be referred to as consumption for "extended" periods.

The term "regular basis" or "regular administration" means at least monthly dosing with the compositions or consumption of the compositions, and in one aspect, means at least weekly dosing. More frequent dosing or consumption, such as twice or three times weekly, can be performed in certain embodiments. Still, in other embodiments, regimens can be used that comprise at least once daily consumption. A frequency, regardless of whether expressly exemplified herein, that allows maintenance of a desired activity level of the measured compound, such as a probiotic, within acceptable ranges can be useful herein. The skilled artisan will appreciate that feeding amounts will be a function of the composition that is being consumed or administered as well as the animal consuming the food, and some food compositions may require more or less frequent administration to maintain a desired activity level of the measured compound (e.g., a probiotic).

The relative terms "improve," "increase," "enhance," "decrease" and the like refer to the effects of the composition disclosed herein (a composition comprising a probiotic and *psyllium*) relative to a composition having a lower amount or lacking such compositional elements, but otherwise identical.

A "blended" composition merely has at least two components having at least one different characteristic relative to each other. In one aspect, moisture content and water activity can be different in the context of the present disclosure. In this regard, description of a composition as "blended" does not imply that the blended composition has been subjected to processing sometimes referenced as "blending," namely mixing components so that they are indistinguishable from each other, and, in one aspect, such processing is avoided when mixing one component with the other components to form a blended composition (e.g., mixing a dry component with a wet or semi-moist component). Further in this regard, in a blended composition each of the at least two components having at least one different characteristic relative to each other can retain their distinct identity and appearance.

"Wet food" means a pet food having a moisture content from about 50% to about 90%, and in one aspect, from about 70% to about 90%. "Dry food" means a pet food having a moisture content less than about 20%, and in one aspect, less than about 15%, and in a specific aspect, less than about 10%. "Semi-moist food" means a pet food having a moisture content from about 20% to about 50%, and in one aspect, from about 25% to about 35%.

"Kibbles" is used synonymously with "chunks" herein and both terms mean pieces of dry or semi-moist pet food which can have a pellet shape or any other shape and can be made by slicing a food composition into separate pieces. Non-limiting examples of kibbles include particulates; pellets; pieces of pet food, dehydrated meat, meat analog, vegetables, and combinations thereof; and pet snacks, such as meat or vegetable jerky, rawhide, and biscuits. A "meat analog" is a meat emulsion product that resembles pieces of natural meat in appearance, texture, and physical structure.

The term "complete and balanced" when referring to a food composition means a food composition that contains all known required nutrients in appropriate amounts and proportions based on recommendations of recognized authorities in the field of animal nutrition, and are therefore capable of serving as a sole source of dietary intake to maintain life or promote production, without the addition of supplemental nutritional sources. Nutritionally balanced pet food and animal food compositions are widely known and widely used in the art, e.g., complete and balanced food compositions formulated according to standards established by the Association of American Feed Control Officials (AAFCO) as of Jan. 1, 2019.

The term "dietary supplement" means a product that is intended to be ingested in addition to a normal diet. Dietary supplements may be in any form, e.g., solid, liquid, gel, tablets, capsules, powder, and the like. In one aspect, they can be provided in convenient dosage forms. In some embodiments, they can be provided in bulk consumer packages such as bulk powders, liquids, gels, or oils. In other embodiments, supplements can be provided in bulk quantities to be included in other food items such as snacks, treats, supplement bars, beverages and the like.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Any embodiment disclosed herein can be combined with any other embodiment disclosed herein unless explicitly and directly stated otherwise.

The present discussion of embodiments, aspects, examples, etc. are independent in that they can apply to all methods and compositions. For example, a probiotic used in a food composition can also be used in the method of improving microbiome of an animal, and vice versa.

Embodiments

The present inventors have discovered that a food composition comprising a probiotic of *Enterococcus* administered with *psyllium* can provide digestive health benefits in an animal including an improved microbiome. One method of determining an improved microbiome includes measuring the *Lactobacillus, Bifidobacteria,* and *Clostridia perfringens* in the microbiome of the animal. Animals administered the presently disclosed compositions can have an increase of *Lactobacillus* and *Bifidobacteria* as well as a decrease of *Clostridia perfringens* as compared to a comparable animal that is not administered the presently disclosed compositions.

As such, in one embodiment, a food composition for an animal, can comprise a probiotic comprising at least one of any suitable strain or subspecies of *Enterococcus*, and *psyllium* in an amount from about 20 weight % to about 80 weight %.

Additionally, a method of improving microbiome within an animal, can comprise administering to the animal a composition comprising a probiotic and *psyllium*, wherein the probiotic comprises at least one of any suitable strain or subspecies of *Enterococcus*.

Generally, the probiotic can be present in the composition in an effective amount such that the animal gains digestive health benefits. In one embodiment, each gram of the composition can contain the probiotic in an amount from about $10^5$ colony forming units (CFU) to about $10^{10}$ CFU. In other embodiments, each gram of the composition can contain from about $10^7$ CFU to about $10^{10}$ CFU or even about $10^7$ CFU to about $10^9$ CFU.

As discussed herein, the health benefits can include enhancing digestive health, treating diarrhea, increasing fecal quality, diversifying the microbiome, increasing beneficial bacteria, e.g., increasing *Lactobacillus* and *Bifidobacteria*, decreasing harmful bacteria, e.g., decreasing *Clostridia perfringens*, or combinations thereof. In one aspect, the health benefit can include complete resolution of diarrhea.

Generally, probiotics can be administered to the animal in amounts of from about one to about twenty billion CFU per day for the healthy maintenance of intestinal microflora, preferably from about 10 million to about 10 billion live bacteria per day.

Generally, the *psyllium* can be present in the composition in an effective amount such that the animal gains digestive health benefits. In one embodiment, the *psyllium* can be present in the composition in an amount of from about 20 weight % to about 80 weight %. In other embodiments, the *psyllium* can be present in an amount from about 30 weight % to about 70 weight %, or even from about 40 weight % to about 60 weight %.

Typically, the present compositions can be administered to the animal for a sufficient time to effect change in the animal's microbiome. In one embodiment, the composition can be administered to the animal on a regular basis. In another embodiment, the composition can be administered long-term. The present compositions are generally food compositions but can also be administered as part of a dietary regime in the form of supplements, treats, sachets, and the like. In one embodiment, the composition is a pet food composition. In another embodiment, the composition is a dietary supplement. In still another embodiment, the composition is a sachet.

Generally, the probiotic can be any suitable strain or subspecies of *Enterococcus*. In one embodiment, the probiotic can comprise *Enterococcus faecium* (SF68® by Cerbios-Pharma SA, also available as the probiotic feed additive Cernivet® LBC ME10 from Cerbios-Pharma SA). As discussed herein, the probiotic can be added to the composition in sufficient amounts to effect a health benefit. In one embodiment, the probiotic can be micro-encapsulated. As such, the probiotics can be microencapsulated within a biocompatible microcapsule to enhance or sustain the viability of the probiotics, particularly during storage. The microcapsule acts as a barrier to protect the probiotics from harmful environmental conditions such as temperature fluctuations, oxygen, moisture, and light. Microcapsules comprise an active agent, e.g., a probiotic core surrounded by a biocompatible shell or coating. Suitable materials for preparation of biocompatible microcapsules and methods for encapsulation are known in the art, see for example, U.S. Pat. No. 6,974,592 to Yan, U.S. Pat. No. 6,969,530 to Curtis et al., U.S. Pat. No. 6,887,493 to Shefer et al. and U.S. Pat. No. 6,303,355 to Opara, and U.S. patent application Ser. No. 10/507,359 to Ubbink et al., and Ser. No. 10/656,386 to Simmons et al., the contents of each are incorporated by reference herein. The microcapsules can be prepared for controlled release of the probiotics after administration to an animal. In preferred embodiments, the microcapsules of the invention range from about 0.1 mm to about 1.0 mm in diameter. In one embodiment, the probiotics are microencapsulated with a biopolymer matrix coated with shellac.

Additionally, the compositions disclosed herein can contain other ingredients. In one embodiment, the compositions can contain other prebiotics. Prebiotics include any substance that alters microflora composition of the gastrointestinal tract by providing a substrate for growth of microorganisms. Prebiotics include, without limitation, natural and synthesized oligosaccharides, soluble fibers, resistant starch, and gums. The oligosaccharides can be linear or branched. The prebiotic can be specifically chosen for its ability to enhance the survival of the probiotic in the storage container, or in the gastrointestinal tract of an animal. The prebiotic can also be specifically chosen for its ability to enhance the functionality of the probiotic in the animal or to complement the benefits of the probiotic. Generally, prebiotics are administered in amounts sufficient to positively stimulate the healthy microflora in the gut and cause these "good" bacteria to reproduce. Typical amounts are from about one to about 10 grams per serving or from about 5 percent to about 40 percent of the recommended daily dietary fiber for an animal.

Generally, the compositions can contain any amount of probiotics needed to achieve a health benefit. For embodiments of dietary supplements, such supplements can comprise from about 1% to about 90% probiotics, from about 1% to about 70% probiotics, or even, from about 1% to about 50% probiotics.

In one embodiment, composition can comprise at least one of animal digest, dried brewers yeast, vitamin C; vitamin E, beta carotene, zinc proteinate, manganese proteinate, ferrous sulfate, copper proteinate, calcium iodate, and sodium selenite. In some embodiments, the composition can include at least two of, at least three of, at least four of, at least five of, or even at east six of: animal digest, dried brewers yeast, vitamin C; vitamin E, beta carotene, zinc proteinate, manganese proteinate, ferrous sulfate, copper proteinate, calcium iodate, and sodium selenite. In another embodiment, the composition can include each one of animal digest, dried brewers yeast, vitamin C; vitamin E, beta carotene, zinc proteinate, manganese proteinate, ferrous sulfate, copper proteinate, calcium iodate, and sodium selenite.

As discussed herein, the present composition can include animal digest. Useful animal digests in the present invention can be any animal digest known to skilled artisans included liquid animal digests and dried animal digests. Such digests include any material that results from chemical and/or enzymatic hydrolysis of clean and undecomposed animal tissue. Additionally, dried brewers yeast can be useful in the present invention, which is any dried brewers yeast known to skilled artisans, e.g., the dried, inactive agent that is a byproduct of the brewing industry. Animal digest and dried brewers yeast have been found to enhance the palatability of the compositions, including dietary supplements and food compositions. When present in such compositions, the animal digest comprises from about 1 weight % to about 90 weight % of the composition and the dried brewers yeast comprises from about 1 weight % to about 30 weight % of the composition.

The vitamin C, vitamin E, beta carotene, zinc proteinate, manganese proteinate, ferrous sulfate, copper proteinate, calcium iodate, and sodium selenite are compounds known to skilled artisans. These compounds have been found to enhance immunity and augment the action of the probiotics in the dietary supplement of the present invention. All of these compounds, the animal digest, and dried brewers yeast have also been found in combination to extend the life of the probiotics compared to the probiotics when not in the compositions. When present in the food composition or supplement, the composition comprises from about 0.1% to about 10% vitamin C, from about 0.1% to about 10% vitamin E, from about 0.01% to about 3% beta carotene, from about 0.1% to about 5% zinc proteinate, from about 0.01% to about 3% manganese proteinate, from about 0.01% to about 3% ferrous sulfate, from about 0.01% to about 1% copper proteinate, from about 0.01% to about 1% calcium iodate, and from about 0.001% to about 0.1% sodium selenite. In a further embodiment, the food composition or dietary supplement further comprises from about 0.1% to about 2% taurine.

Regarding supplements, the dietary supplements can be prepared as a variety of formulations such as a powder, granule, pellet, or any other appropriate delivery form. In some embodiments, the dietary supplement formulation can be powder containing microencapsulated probiotics within a biopolymer matrix. The powder dietary supplement can be sprinkled over or otherwise applied to and admixed with a food or other composition, particularly a pet food such as dog food or cat food. The powder dietary supplements can be specially formulated for consumption by a particular animal, such as companion animal. In one embodiment, the powder dietary supplement comprises a high concentration of probiotics such that the supplement can be administered to the animal in small amounts, or in the alternative, can be diluted before administration to an animal. A skilled practitioner can devise other routes of administration such as providing the dietary supplement alone or feeding it in, on, or with a pet treat.

The dietary supplements can be formulated for storage for prolonged periods at room temperature or, alternatively, can be refrigerated, freeze dried, or frozen. In one embodiment, the dietary supplement can be stored at room temperature and the probiotics in the dietary supplement remain substantially viable for at least 22 days when stored at room temperature. Predictive modeling showed that such probiotics remain substantially viable despite periodic short-term spikes in storage temperature that can exceed room temperature by up to 60° C.

The compositions of the invention can comprise additional substances such as minerals, vitamins, salts, proteins, amino acids, fibers, condiments, colorants, and preservatives. Non-limiting examples of minerals include calcium, phosphorous, potassium, sodium, iron, chloride, boron, copper, zinc, magnesium, manganese, iodine, selenium and the like, and various salts thereof. Non-limiting examples of vitamins include vitamin A, various B vitamins, e.g., niacin, pantothenic acid, folic acid, biotin, vitamin D, and vitamin K. The compositions may also comprise carotenoids such as alpha-carotene, lycopene, lutein, zeaxanthin and beta-cryptoxanthin. Additional ingredients may also be included, for example, inulin, amino acids, and the like. In one specific embodiment, the amino acid can be taurine.

In various embodiments, the compositions of the invention may further comprise from about 15% to about 60% crude protein. In one embodiment, the compositions comprise about 40% to about 55% crude protein. The crude protein material may comprise vegetable proteins such as soybean, corn, rice, cottonseed, and peanut, or animal proteins such as casein, albumin, and meat protein. Non-limiting examples of meat protein useful herein include pork, lamb, equine, poultry, fish, and mixtures thereof.

The compositions may further comprise from about 5% to about 40% fat. In one embodiment, the compositions can comprise about 15% to about 22% fat. The compositions may further comprise a source of carbohydrate. The compositions may comprise from about 15% to about 60% carbohydrate. Non-limiting examples of such carbohydrates include grains or cereals such as rice, corn, sorghum, alfalfa, barley, soybeans, canola, oats, wheat, and mixtures thereof. The compositions may also optionally comprise other materials such as dried whey and other dairy by-products.

The compositions may also further comprise at least one fiber source. The compositions may comprise from about 0.5% to about 5% fiber. A variety of soluble or insoluble fibers may be utilized, as will be known to those of ordinary skill in the art. The fiber source can be beet pulp (from sugar beet), gum arabic, gum talha, *psyllium*, rice bran, carob bean gum, citrus pulp, pectin, fructooligosaccharide, mannanoligofructose, soy fiber, fiber from lupins, arabinogalactan, galactooligosaccharide, arabinoxylan, or mixtures thereof. The fiber source can be a fermentable fiber, as are many of those listed above. Fermentable fiber has previously been described to provide a benefit to the immune system of companion animals. Fermentable fiber or other compositions known to those of skill in the art which provide a prebiotic composition that could enhance the growth of probiotics within the intestine may also be incorporated into the composition to aid in the enhancement of the benefits provided by the present invention to the immune system gastrointestinal system, and general health of an animal.

In some embodiments where the composition is a supplement, to enhance the length of time the supplement can be stored, the dietary supplements can have a total moisture content between about 2% and about 10% by weight of the supplement. In one embodiment, the total moisture content can be less than 5% by weight of the supplement. Similarly, the dietary supplement can have a water activity in the range of 0.20 to 0.6. In one aspect, the water activity can be less than 0.55.

The compositions can be specially formulated for particular animals such as dogs or cats. Similarly, the compositions may be specially formulated for young, adult, or senior animals. In general, specialized formulations comprise ingredients that meet the energy and nutritional requirements appropriate for particular animals and for particular animals at different stages of development or age, or with specific nutrient requirements related to a disease state.

In one embodiment, the compositions can be formulated for dogs. This formula can comprise at least one of the following ingredients: from about 1% to about 90% animal digest, from about 1% to about 30% dried brewers yeast, from about 0.1% to about 10% vitamin C, from about 0.1% to about 10% vitamin E, from about 0.01% to about 3% beta carotene, from about 0.1% to about 5% zinc proteinate, from about 0.01% to about 3% manganese proteinate, from about 0.01% to about 3% ferrous sulfate, from about 0.01% to about 1% copper proteinate, from about 0.01% to about 1% calcium iodate, and from about 0.001% to about 0.1% sodium selenite. In a further embodiment, the compositions further comprises from about 0.1% to about 2% taurine, and from about 1% to about 50% probiotics. The compositions may further comprise from about 0.01% to about 2% sodium chloride.

In another embodiment, the compositions can be formulated for cats. This formula can comprise at least one of the following: from about 0% to about 80% animal digest, from about 0% to about 30% dried brewers yeast, from about 0% to about 10% vitamin C, from about 0% to about 10% vitamin E, from about 0% to about 3% beta carotene, from about 0% to about 5% zinc proteinate, from about 0% to about 2% taurine, from about 0% to about 3% manganese proteinate, from about 0% to about 3% ferrous sulfate, from about 0% to about 1% copper proteinate, from about 0% to about 0.1% calcium iodate, from about 0% to about 0.01% sodium selenite, and from about 1% to about 50% probiotics. The compositions may further comprise from about 0.01% to about 2% sodium chloride.

The skilled artisan can determine the appropriate amount of probiotics to be added to a given formulation. Such factors that may be taken into account include the average consumption of specific types of compositions by different animals, whether the animal that is intended to ingest the dietary supplements has any particular health, wellness, or nutritional requirements, or suffers from a particular disease or disorder, the age, sex, size, or breed of the animal, and the manufacturing conditions under which the composition is prepared. The concentrations of probiotics to be added to the composition can be calculated on the basis of the energy and nutrient requirements of the animal.

The probiotics, particularly the microencapsulated probiotics, in the composition remain substantially viable when the composition is stored for a period of 11 days at temperatures up to 50° C., 2 days at the temperatures up to 60° C., or 20 hours at temperatures up to 65° C.]

Additionally, the composition can further comprise an anti-diarrhea agent.

As discussed herein, in various embodiments, the present compositions can be pet food compositions. In various embodiments, the pet food composition can be a wet food, a semi-moist food or a dry food. In an embodiment, the pet food composition is one or more components of a blended composition. In some embodiments, the pet food composition is a kibble, and in some embodiments, the pet food composition is a meat analog.

The pet food compositions disclosed herein can be any food formulated for consumption by a canine or feline. In an embodiment, the pet food composition can be a complete and balanced pet food; i.e., provides complete nutrition as defined by the Association of American Feed Control Officials (AAFCO) for a canine or feline.

The pet food composition can comprise meat, such as emulsified meat. Examples of suitable meat include poultry, beef, pork, lamb and fish, especially those types of meats suitable for pets. The meat can include any additional parts of an animal including offal. Some or all of the meat can be provided as one or more meat meals, namely meat that has been dried and ground to form substantially uniform-sized particles and as defined by AAFCO. Additionally or alternatively, vegetable protein can be used, such as pea protein, corn protein (e.g., ground corn or corn gluten), wheat protein (e.g., ground wheat or wheat gluten), soy protein (e.g., soybean meal, soy concentrate, or soy isolate), rice protein (e.g., ground rice or rice gluten) and the like.

The pet food compositions disclosed herein can comprise vegetable oil, a flavorant, a colorant and water. Suitable vegetable oils include soybean oil, corn oil, cottonseed oil, sunflower oil, canola oil, peanut oil, safflower oil, and the like. Examples of suitable flavorants include yeast, tallow, rendered animal meals (e.g., poultry, beef, lamb, pork), flavor extracts or blends (e.g., grilled beef), animal digests, and the like. Suitable colorants include FD&C colors, such as blue no. 1, blue no. 2, green no. 3, red no. 3, red no. 40, yellow no. 5, yellow no. 6, and the like; natural colors, such as caramel coloring, annatto, chlorophyllin, cochineal, betanin, turmeric, saffron, paprika, lycopene, elderberry juice, pandan, butterfly pea and the like; titanium dioxide; and any suitable food colorant known to the skilled artisan.

The pet food compositions disclosed herein can optionally include additional ingredients, such as other grains and/or other starches additionally or alternatively to flour, amino acids, fibers, sugars, animal oils, aromas, other oils additionally or alternatively to vegetable oil, humectants, preservatives, polyols, salts, oral care ingredients, antioxidants, vitamins, minerals, probiotic microorganisms, bioactive molecules or combinations thereof.

Suitable starches include a grain such as corn, rice, wheat, barley, oats, soy and the like, and mixtures of these grains, and can be included at least partially in any flour. Suitable humectants include salt, sugars, propylene glycol and polyhydric glycols such as glycerin and sorbitol, and the like. Suitable oral care ingredients include alfalfa nutrient concentrate containing chlorophyll, sodium bicarbonate, phosphates (e.g., tricalcium phosphate, acid pyrophosphates, tetrasodium pyrophosphate, metaphosphates, and orthophosphates), peppermint, cloves, parsley, ginger and the like. Examples of suitable antioxidants include butylated hydroxyanisole ("BHA") and butylated hydroxytoluene ("BHT"), vitamin E (tocopherols), and the like.

Non-limiting examples of vitamins that can be used include Vitamins A, B-complex (such as B-1, B-2, B-6 and B-12), C, D, E and K, niacin and acid vitamins such as folic acid and biotin. Non-limiting examples of suitable minerals include calcium, iron, zinc, magnesium, iodine, copper, phosphorus, manganese, potassium, chromium, molybdenum, selenium, nickel, tin, silicon, vanadium, boron and the like.

Non-limiting examples of suitable preservatives include potassium sorbate, sorbic acid, sodium methyl para-hydroxybenzoate, calcium propionate, propionic acid, and combinations thereof.

Specific amounts for each additional ingredient in the pet food compositions disclosed herein will depend on a variety of factors such as the ingredient included in the first edible material and any second edible material; the species of animal; the animal's age, body weight, general health, sex, and diet; the animal's consumption rate; the purpose for which the food product is administered to the animal; and the like.

EXAMPLES

The following non-limiting examples are illustrative of embodiments of the present disclosure.

Example 1—In Vitro Study

To simulate effects in the large bowel, *psyllium* and *psyllium*/SF68® were evaluated in a canine and feline batch in vitro fermentation model. In vitro analysis: substrates were fermented for 0 and 12 hours with the fecal inoculum obtained from multiple dogs or cats. Freshly voided feces from dog and cat donors was collected and immediately frozen at −80° C. and used to inoculate all substrate x time combinations in triplicate. Triplicate tubes containing no substrate also were fermented with each inoculum source and time point to account for appropriate corrections not arising from the substrates themselves (e.g., blank). Aliquots of a semidefined medium, added to maintain microbial viability, were aseptically transferred into 50-mL tubes containing 300 mg of substrate. Anaerobic conditions were maintained by sealing the tubes with rubber stoppers equipped with 1-way gas release valves. Fecal samples were pooled and then diluted 1:10 (wt/vol) in anaerobic dilution solution by blending it for 15 seconds in a Ninja blender under a stream of $CO_2$. Blended, diluted feces were filtered through 4 layers of cheesecloth and sealed in 125-mL serum bottles under $CO_2$. Aliquots of fecal inoculum were anaerobically injected into the media+substrate tubes and incubated for 12 hours, after which sub-samples of each were taken for analysis. Measurements of pH, short chain fatty acids, and targeted microbiota via qPCR (*Bifidobacterium* spp., *Lactobacillus* spp., *C. perfringens*) were corrected by blank and 0 hour tubes. Microbiome analysis via 16S Illumina sequencing was not blank corrected, rather compared to 0 hour timepoint.

Results were obtained. pH was decreased with the *psyllium*/SF68® combination compared to *psyllium* alone and blank, indicating microbial fermentation, SCFA and lactate production, and a more suitable environment for beneficial colonic bacteria. *Lactobacillus* spp. increased for both *psyllium* and *psyllium*/SF68® compared to blank. *Bifidobacteria* spp. increased with the *psyllium*/SF68® blend compared to blank and *psyllium* alone. Increases in *Lactobacillus* and *Bifidobacterium* spp. are indicative of good digestive health. *Psyllium* alone increased *Clostridia perfringens* compared to blank, the combination of *psyllium*/SF68® did not. *C. perfringens* is a pathogenic bacteria, and increases indicate the potential for poor digestive health. Based on 16S Illumina sequencing methodology, fermentation of *psyllium*/SF68 led to a clear separation in bacteria patterns. LEfSE analysis showed that *Faecalibacterium* and *Lactobacillus* are more associated with the *psyllium*/SF68 blend in the cat, while *Lactobacillus, Bifidobacterium*, and *Faecalibacterium* were more associated with the *psyllium*/SF68® blend in dog. These bacteria are indicators of good digestive health. Overall, these in vitro results indicated that the *psyllium*/SF68® blend stimulates the growth of specific bacteria to support digestive health.

Example 2—In Vivo Dog Study

A field study with Alaskan Huskies from various sled dog kennels in the Fairbanks, Ak. area, including the Nestle Purina kennel facility in Salcha, Ak. was performed to test efficacy. In this study, dogs with identified acute diarrhea, were supplemented with 1 of 5 treatments for 7 days, during which, fecal scores were recorded by owners using a scale of 1-3. The treatments and components are shown in Table 1:

TABLE 1

| Treatment | Animal Digest (g) | SF68 ® (g) | Egg Powder (g) | Psyllium (g) |
|---|---|---|---|---|
| 1. Control | 0.78 | — | — | — |
| 2. SF68 ® | 0.78 | 0.05 | — | — |
| 3. SF68 ® + Egg | 0.78 | 0.05 | 1.0 | — |
| 4. SF68 ® + Psyllium | 0.78 | 0.05 | — | 0.5 |
| 5. SF68 ® + Egg + Psyllium | 0.78 | 0.05 | 1.0 | 0.5 |

By day 7, all treatments provided better fecal scores than the control. Additionally, complete resolution of diarrhea was studied for the treatments. Unexpectedly, treatment #4 provided the highest incidence of complete resolution. Notably, treatment #2 (SF68®) provided higher incidence of complete resolution than control, while treatment #3 (SF68®+egg powder) was even higher, and treatment #5 (SF68®+*psyllium*+egg powder) was still even higher (than #2 or #3). However, surprisingly, the highest incidence of complete resolution was achieved by treatment #4 (SF68®+*psyllium*). This was unexpected as the egg powder showed an increased effect when paired with SF68® and the addition of *psyllium* showed an even better result. As such, the removal of the egg powder was expected to lower the incidence of complete resolution. Such a finding was not expected nor predicted. The results are shown in Table 2.

TABLE 2

| | Treatment | | | | |
|---|---|---|---|---|---|
| | Control | SF68 ® | SF68 ® + Egg | SF68 ® + Egg + Psyllium | SF68 ® + Psyllium |
| Complete Resolution (Mean, scored as 0 or 1) | 0.39 | 0.45 | 0.55 | 0.59 | 0.64 |

As such, in one embodiment, the present compositions can consist essentially of a probiotic and *psyllium*, wherein the probiotic comprises at least one of any suitable strain or subspecies of *Enterococcus*. In one aspect, the compositions can consist of the *psyllium* and the probiotic. In another aspect, the compositions can exclude egg powder.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of improving a microbiome within an animal, the method comprising: administering to the animal a therapuetically effective amount of a composition comprising a probiotic and the prebiotic *psyllium*, wherein the *psyllium* is about 20 weight % to about 80 weight % of the composition, and wherein the probiotic comprises at least one strain or subspecies of an *Enterococcus* sp.

2. The method of claim 1, wherein each gram of the composition contains the probiotic in an amount from about $10^5$ colony forming units (CFU) to about $10^{10}$ CFU.

3. The method of claim 1, wherein the psyllium is present in the composition in an amount of from about 40 weight % to about 60 weight %.

4. The method of claim 1, wherein the composition is administered to the animal on a regular basis.

5. The method of claim 1, wherein the composition is a pet food composition.

6. The method of claim 1, wherein the composition is a dietary supplement.

7. The method of claim 1, wherein the probiotic comprises *Enterococcus faecium*.

8. The method of claim 1, wherein the administration increases the level of at least one *Lactobacillus* sp. and at least one *Bifidobacterium* sp.

9. The method of claim 1, wherein the administration decreases the level of *Clostridium perfringens*.

10. The method of claim 1, wherein the administration enhances digestive health, treats diarrhea, increases fecal quality, or combinations thereof.

11. The method of claim 1, wherein the psyllium is about 30 weight % to about 70 weight % of the composition.

12. The method of claim 1, wherein the animal is a dog or a cat.

13. The method of claim 1, wherein the composition is administered to the animal long-term on a regular basis.

14. The method of claim 1, wherein the composition comprises microcapsules which contain the probiotic and have a diameter from about 0.1 mm to about 1.0 mm.

15. The method of claim 1, wherein the composition further comprises about 0.1% to about 10% vitamin C, about 0.1% to about 10% vitamin E, about 0.01% to about 3% beta carotene, about 0.1% to about 5% zinc proteinate, about 0.01% to about 3% manganese proteinate, about 0.01% to about 3% ferrous sulfate, about 0.01% to about 1% copper proteinate, about 0.01% to about 1% calcium iodate, and about 0.001% to about 0.1% sodium selenite.

16. The method of claim 15, wherein the composition further comprises about 0.1% to about 2% taurine.

17. The method of claim 1, wherein the composition further comprises an additional prebiotic, the additional prebiotic selected from the group consisting of natural oligosaccharides, synthesized oligosaccharides, soluble fibers, resistant starch, and gums.

18. The method of claim 1, wherein the *psyllium* is the only prebiotic in the composition.

19. The method of claim 1, wherein the composition consists essentially of the probiotic and the *psyllium*.

* * * * *